(12) United States Patent
Morel

(10) Patent No.: US 8,703,987 B2
(45) Date of Patent: Apr. 22, 2014

(54) METHODS FOR PREPARING 2-METHOXYISOBUTYLISONITRILE AND TETRAKIS(2-METHOXYISO-BUTYLISONITRILE)COPPER(I) TETRAFLUOROBORATE

(75) Inventor: Pierre Morel, Pierrefonds (CA)

(73) Assignee: Draximage Limited, Dublin (IE)

( * ) Notice: Subject to any disclaimer, the term of this patent is extended or adjusted under 35 U.S.C. 154(b) by 0 days.

(21) Appl. No.: 12/505,054

(22) Filed: Jul. 17, 2009

(65) Prior Publication Data

US 2010/0010250 A1    Jan. 14, 2010

Related U.S. Application Data

(62) Division of application No. 11/754,638, filed on May 29, 2007, now Pat. No. 7,563,920.

(60) Provisional application No. 60/863,424, filed on Oct. 30, 2006.

(51) Int. Cl.
C07C 249/00    (2006.01)

(52) U.S. Cl.
USPC ...................................................... 558/302

(58) Field of Classification Search
USPC ........................................................ 558/302
See application file for complete search history.

(56) References Cited

U.S. PATENT DOCUMENTS

| | | | | |
|---|---|---|---|---|
| 1,968,032 | A | * | 7/1934 | Edlund .......................... 568/648 |
| 4,864,051 | A | | 9/1989 | Ramalingham |
| 4,988,827 | A | | 1/1991 | Bergstein et al. |
| 5,210,270 | A | * | 5/1993 | Te-Wei et al. .................. 558/302 |
| 5,346,995 | A | | 9/1994 | Te-Wei et al. |

FOREIGN PATENT DOCUMENTS

| | | |
|---|---|---|
| CZ | 286794 | 7/2000 |
| DD | 300742 | 7/1990 |
| EP | 233368 | 8/1987 |
| EP | 546233 | 6/1993 |
| GB | 2222403 | 3/1990 |
| RU | 2026857 | 1/1995 |
| SK | 279625 | 1/1999 |
| SK | 280287 | 11/1999 |

OTHER PUBLICATIONS

Fabiano et al. Synthesis, 1987, p. 190-192.*
Zykov et al. Journal of Radioanalytical & Nuclear Chemistry 221 (1-2), 1997, 227-229.*
Mitsunobu, Synthesis 1981; 1981: 1-28.*
Organic Preparations and Procedures International (1989), 21(4), 511-14.*
Winstein, et al., "Neighboring Carbon and Hydrogen. XV. Rearrangement as a Sequel to Neighboring Functional Group Participation. Solvolysis of 2-Methyl-2-methoxy-1-propyl p-Bromobenzenesulfonate," Journal of the American Chemical Society, vol. 75, No. 1, 1953, p. 155-158.
Winstein, et al., "The Role of Neighboring Groups in Replacement Reactions. XVIII. Migration of the Methoxyl Group," Journal of the American Chemical Society, vol. 74, No. 5, 1952, p. 1160-1164.
Te-Wei, et al., "Synthesis, Reactivity and $^{99m}$Tc Labelling of 2-Alkoxyisobutylisonitrile," Applied Radiation & Isotopes, vol. 47. No. 2, 1996, p. 207-210.
Ferro-Flores, et al., "An Improved Procedure for the Synthesis of 2-Methoxyisobutylisonitrile: An Efficient Complexing Agent for $^{99m}$Tc," Journal of Radioanalytical & Nuclear Chemistry, vol. 188, No. 6, 1994, p. 409-415.
Ramalingham, K., "Facile Synthesis of 2-Methoxyisobutylisonitrile," Organic Preparations & Procedures International, vol. 21, No. 4, 1989, p. 511-514.
Tarbell, et al., "Acid-catalyzed Ring-opening Reactions of Some Unsymmetrical Ethyleneimine Derivatives," Journal of the American Chemical Society, vol. 72, 1950, p. 2657-61.
Thipyapung, et al., "Synthesis of Tetrakis(2-methoxyisobutylisocyano)copper(I)tetrafluoroborate via Condensation of Acetone with Nitromethane," Journal of Scientific Research Chulalongkom University. vol. 28, No. 2, 2003, p. 111-118.
Harder, et al., The Action of Alcohols on Ethylenimines (aziridines). Synthesis of β-amino Ethers, University Marburg, Germany Ber., 1964, 97(2), p. 510-19. *Abstract Only*.
Clapp, et al., "Reactions of Ethylenimines. VI. Picrates," Journal of the American Chemical Society, vol. 77, 1955, p. 5116-5118.
Luo, et al., The Journal of Nuclear and Radiochemistry, vol. 14, No. 1 1992, p. 44-48, 58.
Zykov et al., "Preparation of a Ready-for-Injection Radiopharmaceutical Based on MIBI using $^{99m}$Tc from a Centralized Extraction Generator," Journal of Radioanalytical & Nuclear Chemistry, vol. 221, No. 1-2, 1997, p. 227-229.
IAEA-TECDOC-532 , 1989.
IAEA-TECDOC-805 , 1995.
Van Wyk; et al., "Synthesis and $^{99m}$Tc Labelling of MMI (MIBI) and its Ethyl Analogue EMI," Applied Radiation & Isotopes, vol. 42, No. 7, 1991, p. 687-689.
Lima, et al., "Preparation and Evaluation of Modified Composition for Lyophilized Kits of [Cu(MIBI)$_4$]BF$_4$ for [$_{99m}$Tc] Technetium Labeling," Brazilian Archives of Biology and Technology, vol. 48, 2005, p. 1-8.
Porcheddu, et al., "Microwave-Assisted Synthesis of Isonitriles: A General Simple Methodology," Journal of Organic Chemesitry, vol. 70, 2005, p. 2361-2363.
Deicas, et al., "Synthesis, Characterization and Spectroscopic Properties of [Cu$^1$(alkylisocyanide)$_4$]BF$_4$ Complexes. X-ray Crystal Structures of [Cu(MIBI)$_4$]BF$_4$ and [Cu(CPI)$_4$]BF$_4$." Polyhedron, vol. 16, No. 14, 1997, p. 2397-2403.
Kirmse, et al. "Reaktionen der Beta-Alkoxyalkyl-Carbene." Chem. Ber., vol. 100, 1967, pp. 1491-1506.
Fabiano, et al. "A Simple conversion of Alcohols into Amines." Synthesis, No. 2, 1987, pp. 190-192.
Mansue, et al. Fractionation of lyophilized MIBI kit for 99mTc labeling, Journal of Radioanalytical and Nuclear chemistry, vol. 268, No. 1, 2006.

* cited by examiner

*Primary Examiner* — Nizal Chandrakumar
(74) *Attorney, Agent, or Firm* — Blank Rome LLP

(57) ABSTRACT

The present invention relates to new synthetic methods for preparing 2-methoxyisobutylisonitrile and metal isonitrile complexes, such as tetrakis(2-methoxyisobutylisonitrile) copper(I) tetrafluoroborate, which are used in the preparation of technetium ($^{99m}$Tc) Sestamibi, and novel intermediate compounds useful in such methods.

5 Claims, No Drawings

METHODS FOR PREPARING 2-METHOXYISOBUTYLISONITRILE AND TETRAKIS(2-METHOXYISO-BUTYLISONITRILE)COPPER(I) TETRAFLUOROBORATE

This application is a divisional of U.S. patent application Ser. No. 11/754,638, filed May 29, 2007, which claims the benefit of U.S. Provisional Application No. 60/863,424, filed Oct. 30, 2006, both of which are hereby incorporated by reference.

FIELD OF THE INVENTION

The present invention relates to new syntheses of 2-methoxyisobutylisonitrile and metal isonitrile complexes, such as tetrakis(2-methoxyisobutylisonitrile)copper(I) tetrafluoroborate, which are used in the preparation of technetium ($^{99m}$Tc) Sestamibi.

BACKGROUND OF THE INVENTION

Methoxyisobutylisonitrile (MIBI) is a key starting material in the preparation of the complex technetium ($^{99m}$Tc) hexakis (2-methoxyisobutylisonitrile) (technetium ($^{99m}$Tc) Sestamibi). This radiopharmaceutical, which is commercially available in the form of a kit under the tradenames CARDIOLITE® and MIRALUMA®, is useful for detecting coronary artery disease as well as evaluating breast lesions by planar imaging. Discovered in 1981 by Alan Davison, it received FDA approval in 1990 and it has been sold commercially since February 1991.

The kit includes a lyophilized mixture of a copper complex of MIBI (tetrakis(2-methoxyisobutylisonitrile)copper(I) tetrafluoroborate ([Cu(MIBI)$_4$]BF$_4$)) as the active ingredient, sodium citrate dihydrate as a buffer, L-cysteine hydrochloride monohydrate as a stabilization aid, mannitol as a lyophilization aid, and stannous chloride dihydrate as a reducing agent. Prior to use, the lyophilized mixture is reconstituted with sodium pertechnetate ($^{99m}$Tc) and boiled to form technetium ($^{99m}$Tc) Sestamibi. The U.S. Pharmacopoeia (29$^{th}$ Ed.) requires that a mean of not less than 90% (corrected area percentage) of the total radioactivity is represented by $^{99m}$Tc-Sestamibi, and a mean of not more than 5% (corrected area percentage) of the total radioactivity is present as $^{99m}$Tc pentamibi dimethylvinyl isonitrile.

The synthesis of MIBI has been extensively studied over the past twenty five years. It is not readily achieved because there is no commercially available chemical having a related structure. Prior methods of preparing MIBI are described in U.S. Pat. Nos. 4,864,051, 4,988,827, 5,210,270 and 5,346,995.

However, there is a continuing need for improved methods of preparing MIBI and metal complexes thereof, such as [Cu(MIBI)$_4$]BF$_4$.

SUMMARY OF THE INVENTION

The present invention is directed to new methods of preparing 2-methoxyisobutylisonitrile (MIBI) and metal isonitrile complexes, such as tetrakis(2-methoxyisobutylisonitrile)copper(I) tetrafluoroborate ([Cu(MIBI)$_4$]BF$_4$), and novel compounds useful in their preparation.

One aspect of the invention is a method of preparing MIBI by
(a) converting 2,2-dimethyloxirane to 2-methoxyisobutanol (MIBOL),
(b) converting MIBOL to 2-methoxyisobutylamine (MIBA), and
(c) converting MIBA to MIBI.

Another aspect of the invention is a method of preparing MIBI by
(a) converting a compound of the formula

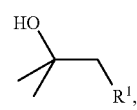

(1)

where R$^1$ is a leaving group, to N-(2-hydroxyisobutyl)-phthalimide (2)

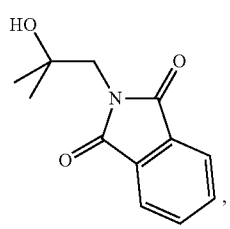

(2)

(b) alkylating compound (2) to form N-(2-methoxyisobutyl)-phthalimide (3)

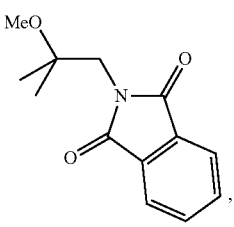

(3)

(c) converting compound (3) to MIBA, and
(d) converting MIBA to MIBI.

According to yet another aspect of the invention, MIBI is prepared by
(a) converting MIBA to a compound of the formula

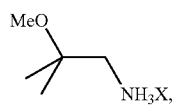

(4)

where X is halogen,
(b) converting the compound of formula (4) to a compound of the formula

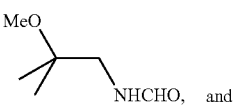

(5)

(c) converting the compound of formula (5) to MIBI.

MIBA in step (a) can be prepared by the methods described above or by alternative methods known in the art, such as those described below.

Yet another aspect of the invention is an intermediate compound selected from:

(a)

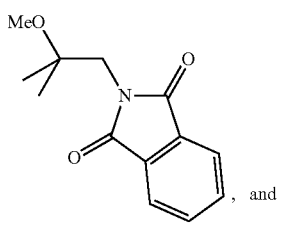
, and (3)

(b)

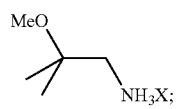

(4)

where X is halogen and preferably Cl.

In another aspect of the invention, MIBI prepared by any of the methods of the present invention is incorporated into a metal isonitrile complex by mixing it with a displaceable metal, such as Cu, Mo, Pd, Co, Ni, Cr, Ag or Rh. A preferred metal isonitrile complex is tetrakis(2-methoxyisobutylisonitrile)copper(I) tetrafluoroborate. The displaceable metal in the metal isonitrile complex may later be replaced by $^{99m}$Tc to form a $^{99m}$Tc isonitrile complex, such as $^{99m}$Tc-Sestamibi.

Another aspect of the invention is a method of preparing tetrakis(2-methoxyisobutylisonitrile)copper(I) tetrafluoroborate (CuMIBI) from MIBI by thermal heating of cuprous chloride and MIBI at about atmospheric pressure and performing an anion exchange reaction with a tetrafluoroborate salt to obtain CuMIBI.

MIBI prepared by any of the methods of the present invention can be incorporated into a kit for preparing technetium ($^{99m}$Tc) Sestamibi. MIBI is preferably incorporated into the kit as a copper complex, such as tetrakis(2-methoxyisobutylisonitrile)copper(I) tetrafluoroborate. For instance, the kit can include a vial containing a lyophilized form of a copper MIBI complex and optionally, one or more additives. Suitable additives include, but are not limited to, buffers (e.g., sodium citrate dihydrate), stabilization aids (e.g., L-cysteine hydrochloride monohydrate), lyophilization aids (e.g., mannitol) and reducing agents (e.g., stannous chloride dihydrate). The technetium radiopharmaceutical can be prepared by adding a non-pyrogenic solution of sodium pertechnetate ($^{99m}$Tc) into the vial and boiling the mixture (such as water bath) for at least 10 minutes.

Yet another aspect of the invention is 99 mTc-Sestamibi containing no quantifiable amount of $^{99m}$Tc-pentamibi dimethylvinyl isonitrile as measured by the method described in the United States Pharmacopoeia (29$^{th}$ Ed.) with a ⅛" lead shielding for the NaI detector of the gamma detector.

Yet another aspect of the invention is a formulation including tetrakis(2-methoxyisobutylisonitrile)copper(I) tetrafluoroborate, sodium citrate dihydrate, L-cysteine hydrochloride monohydrate, mannitol, and stannous chloride dihydrate under an inert gas (such as nitrogen) in a lyophilized vial, wherein the tetrakis(2-methoxyisobutylisonitrile) copper(I) tetrafluoroborate is sufficiently pure so that when the formulation is (i) reconstituted with sodium pertechnetate ($^{99m}$Tc) for injection in saline obtained from the elution of a $^{99}$Mo/$^{99m}$Tc generator and (ii) sufficiently heated to form $^{99m}$Tc-Sestamibi, the $^{99m}$Tc-Sestamibi contains no quantifiable amount of $^{99m}$Tc-pentamibi dimethylvinyl isonitrile as measured by the method described in the United States Pharmacopoeia (29$^{th}$ Ed.) with a ⅛" lead shielding for the NaI detector of the gamma detector. Typically, the $^{99m}$Tc-Sestamibi is cooled to room temperature before measuring the radiochemical purity and the content of $^{99m}$Tc-pentamibi dimethylvinyl isonitrile.

DETAILED DESCRIPTION OF THE INVENTION

Definitions

As used herein, the term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl).

The term "leaving group" as used herein refers to a functional group or atom, which can be displaced by another functional group or atom in a substitution reaction, such as a nucleophilic substitution reaction. Suitable leaving groups include, but are not limited to, chloro, bromo and iodo groups.

The term "MIBOL" as used herein refers to 2-methoxyisobutanol, which has the formula

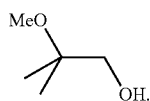

The term "MIBA" as used herein refers to 2-methoxyisobutylamine, which has the formula

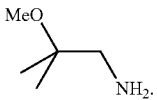

The term "MIBAHCl" as used herein refers to 2-methoxyisobutylamine hydrochloride, which has the formula

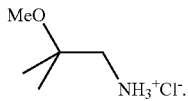

The term "MIBF" as used herein refers to N-(2-methoxyisobutyl)formamide, which has the formula

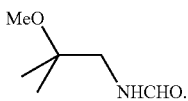

The term "MIBI" as used herein refers to 2-methoxyisobutylisonitrile, which has the formula

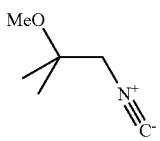

The term "CuMIBI" as used herein refers to tetrakis(2-methoxyisobutylisonitrile)copper(I) tetrafluoroborate, which has the formula $[Cu(MIBI)_4]BF_4$.

A. Methods of Preparing 2-methoxyisobutanol (MIBOL)

2-methoxyisobutanol can be prepared from 2,2-dimethyloxirane (also called isobutylene oxide) by electrophilic addition of methanol on the quaternary carbon of the oxirane ring in the presence of a catalytic amount of acid, such as sulfuric acid. Winstein et al. (*J. Am. Chem. Soc.*, 1952, 75(1), 155-158; *J. Am. chem. Soc.*, 1952, 74(5), 1160-1164) reported performing this reaction by adding methanol and acid to the 2,2-dimethyloxirane. The Winstein reaction proceeds violently, and the exothermicity must be carefully monitored by controlling the rate of addition of acid. The reaction yields 69% on a 72 g scale of 2,2-dimethyloxirane. The present inventor discovered that the reaction can be drastically improved by reversing the sequence of addition of the reagents. By adding 2,2-dimethyloxirane to the mixture of acid and methanol, the reaction proceeds with almost no exothermicity and ensures high yield (90% on a 150 g scale of 2,2-dimethyloxirane). The reaction is preferably quenched, for example, by neutralizing the acid with a potassium hydroxide solution in methanol. MIBOL can be isolated and/or purified by methods known in the art. For example, MIBOL can be isolated by the distillation of the MIBOL-containing solution at atmospheric pressure. This reaction can be readily and safely scaled up.

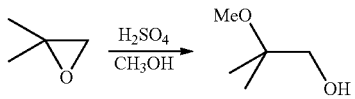

B. Methods of Preparing 2-Methoxyisobutylamine (MIBA)

1. Preparation of MIBA from MIBOL

MIBA can be formed from MIBOL proceeding either with a Mitsunobu reaction (via a phthalimide intermediate) or a Mitsunobu/Staudinger reaction (going through an azide intermediate). The reaction can proceed without having to purify the phthalimide intermediate (or azide intermediate, depending on which reaction is used).

According to one embodiment using a Mitsunobu reaction, MIBOL is converted to MIBA by (i) reacting MIBOL with triphenylphosphine, phthalimide (Phth), and diethylazodicarboxylate (DEAD) or diisopropylazodicarboxylate (DIAD), preferably in THF, to form N-(2-methoxyisobutyl)-phthalimide having the formula

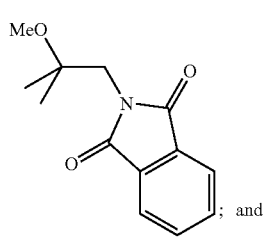

(ii) reacting compound (3) with hydrazine, preferably in methanol, to cleave off the phthalimide leaving group and form MIBA. According to one preferred embodiment, compound (3) is not purified before proceeding to step (ii).

This primary amine (MIBA) can be isolated by methods known in the art. For example, the MIBA can be purified as follows. The hydrazinolysis is quenched with hydrochloric acid and MIBA gets protonated to the hydrochloride salt. After evaporation to dryness, MIBAHCl is extracted from the crude product, for example, by triturating in hydrochloric acid (e.g., 1N HCl). The aqueous solution is extracted with ethyl acetate, and then it is basified, preferably, with sodium hydroxide to a pH of about 12. MIBA is extracted with diethyl ether in a liquid-liquid extraction and isolated by distillation at atmospheric pressure.

The reaction generates phthalidrazide, diisopropyl hydrazinodicarboxylate (or diethyl hydrazinodicarboxylate) and triphenylphosphine oxide as solid wastes and can be safely scaled-up. The reaction is shown below.

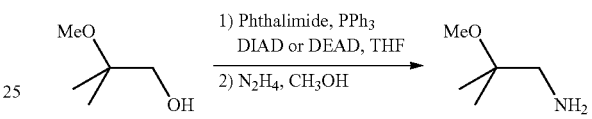

According to one embodiment using a Mitsunobu/Staudinger reaction, MIBOL is converted to MIBA by (i) reacting MIBOL with triphenylphosphine, hydrazoic acid, diethylazodicarboxylate (DEAD) or diisopropylazodicarboxylate (DIAD), preferably in THF, to form 2-methoxyisobutylazide having the formula

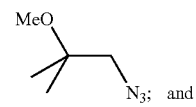

(ii) reacting the compound from step (i) with first triphenylphosphine then water to reduce the azide group and form MIBA. The reaction is shown below.

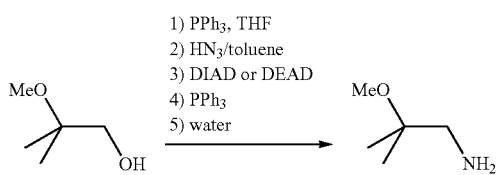

According to one preferred embodiment, compound (4) is not purified before proceeding to step (ii).

2. Preparation of MIBA from 1-chloro-2-methyl-propan-2-ol

MIBA can be formed from commercially available 1-chloro-2-methyl-propan-2-ol. For example, 1-chloro-2-methyl-propan-2-ol can be engaged in a Gabriel reaction using potassium phthalimide (KPhth) and preferably a catalytic amount of sodium iodide (e.g., in dimethylformamide) to form N-(2-hydroxyisobutyl)-phthalimide. The tertiary alcohol is then methylated, for example, using dimethylcarbonate, to form N-(2-methoxyisobutyl)-phthalimide. The phthalimide group is then cleaved off by hydrazinolysis, for example, in methanol, to form MIBA. MIBA can be isolated and/or purified by any method known in the art. For example, MIBA can be isolated in a similar purification process as described above for the Mitsunobu reaction: acidification, evaporation to dryness, trituration in hydrochloric acid, extraction of organic impurities, basification, liquid-liquid extraction and distillation of MIBA.

The reactions are shown below.

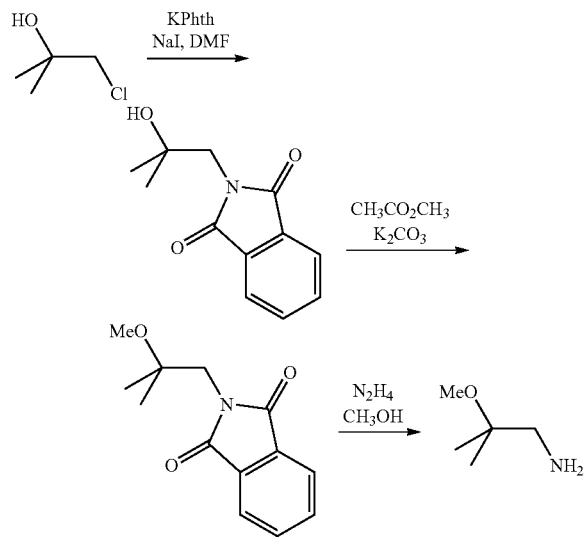

3. Alternative Methods of Preparing MIBA

Other methods of preparing MIBA are described in U.S. Pat. Nos. 4,864,051, 4,988,827, 5,210,270, and 5,346,995; European Patent No. 233368; Te-Wei et al., *Appl. Radiat. Isot.*, 1996, 47(2), 207-210; Ferro-Flores et al., *J. Radioanal. Nucl. Chem.*, 1994, 188(6), 409; K. Ramalingham, *Org. Prep. Proced. Int.*, 1989, 21(4), 511-514; GB Patent Publication Nos. 2222403(A1) and 2222403(B2), Russian Patent No. 2026857; Tarbell, *J. Am. Chem. Soc.*, 1950, 72, 2657-61; German Democratic Republic Patent Publication No. 300742; Slovakian Patent No. 279625; Thipyapung et al., *J. Scient. Res. Chulalongkorn Univ.*, 2003, 28(2), 111-118; Harder, *University Marburg, Germany Ber.*, 1964, 97(2), 510-19; Clapp et al., *J. Am. Chem. Soc.*, 1955, 77, 5116-5118; Luo et al., *He Huaxe Yu Fangshe Huasue*, 1992, 14(1), 44-48, 58, all of which are hereby incorporated by reference.

Those methods are described in detail below.

a. Alternative Method 1

MIBA can be prepared from commercially available 2-hydroxyisobutyronitrile (6). The tertiary alcohol of cyanohydrin (6) is methylated to form 2-methoxyisobutyronitrile (7). Preferably, the methylation if performed in anhydrous methanol in the presence of freshly fused $ZnCl_2$. Suitable reaction conditions are described in U.S. Pat. No. 4,864,051; Ramalingham, *Org. Prep. Proced. Int.*, 1989, 21(4), 511-514; GB Patent Publication Nos. 2222403(A1) and 2222403(B2); German Democratic Republic Patent Publication No. 300742; Slovakian Patent No. 279625 and Zykov et al., *J. Radioanal. Nucl. Chem.*, 1997, 221(1-2), 227-229.

The nitrile group of 2-methoxyisobutyronitrile (6) is reduced, for example, with lithium aluminum hydride preferably in diethyl ether, to form MIBA. Suitable reaction conditions are described in U.S. Pat. No. 4,864,051; Ramalingham, *Org. Prep. Proced. Int.*, 1989, 21(4), 511-514; GB Patent Publication Nos. 2222403(A 1) and 2222403(B2); German Democratic Republic Patent Publication No. 300742; Slovakian Patent No. 279625; Luo et al., *He Huaxe Yu Fangshe Huasue*, 1992, 14(1), 44-48, 58 and Zykov et al., *J. Radioanal. Nucl. Chem.*, 1997, 221(1-2), 227-229.

The reactions are shown below.

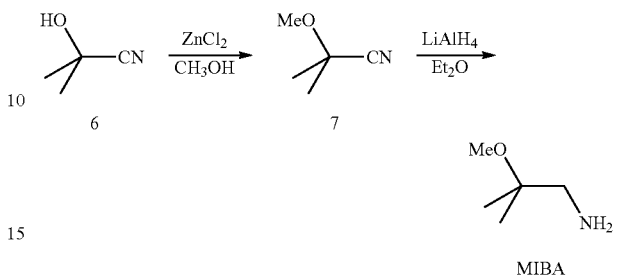

b. Alternative Method 2

MIBA can be prepared from commercially available 2-amino-2-methyl-propan-1-ol (8). The aminoalcohol (8) can undergo an intramolecular cyclization to form 2,2-dimethylaziridine (9), for example, upon reaction with sulfuric acid (and more preferably an equimolar amount of sulfuric acid). Suitable conditions for this reaction are described in U.S. Pat. No. 4,988,827 and European Patent No. 233368. The aziridine (9) is opened with an alcohol (e.g., methanol), preferably in the presence of an acid catalyst (e.g., a Lewis acid, such as boron-trifluoride-bis-methanol), to give a mixture of two amines from which MIBA can be isolated, for example, by distillation. Suitable conditions for this reaction are described in U.S. Pat. No. 4,988,827, European Patent No. 233368, and Harder, *University Marburg, Germany Ber.*, 1964, 97(2), 510-519. Alternatively, 2,2-dimethylaziridine (9) can be reacted with picric acid in methanol to form 2-methoxyisobutylammonium picrate, which can be freed of picrate, for example, by reacting with hydrochloric acid to form 2-methoxyisobutylammonium chloride, which can then be reacted with a base (e.g., sodium methoxide) to form the free amine, MIBA. Suitable conditions for this reaction are described in Clapp et al., *J. Am. Chem. Soc.*, 1955, 77, 5116-5118. The reactions are shown below.

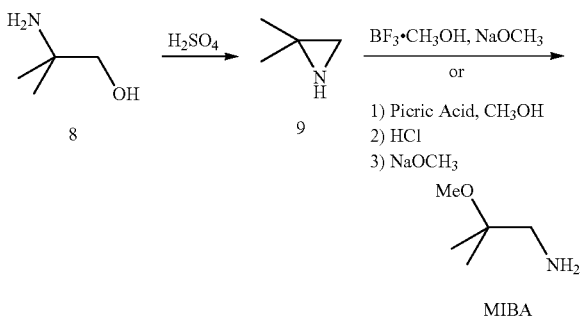

c. Alternative Method 3

MIBA can be prepared from commercially available isobutylene. The alkene (10), which is a gas, is subjected to haloalkoxylation (e.g., by reacting with N-iodosuccinimide or N-bromosuccinimide) to produce 2-methoxyisobutylhalide (e.g., 2-methoxyisobutyliodide or 2-methoxyisobutylbromide) (11). Halide (11) is then reacted in a Gabriel reaction (e.g., nucleophilic substitution with potassium phthalimide followed by hydrazinolysis) to form MIBA.

Suitable conditions for these reactions are described in U.S. Pat. Nos. 5,210,270 and 5,346,995, European Patent No. 546233(B1), and Te-Wei et al., *Appl. Radial. Isot.*, 1996, 47(2), 207-210. The reactions are shown below.

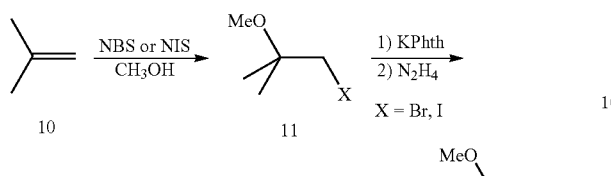

d. Alternative Method 4

MIBA can be prepared from commercially available methyl 2-hydroxyisobutyrate (12). It is methylated, for example, using sodium hydride and iodomethane, to form methyl 2-methoxyisobutanoate (13). Suitable reaction conditions are described in U.S. Pat. No. 4,988,827 and European Patent No. 233368. Methyl 2-methoxyisobutanoate (13) has also been reported to form from a reaction between acetone and chloroform in methanol. Suitable reaction conditions are described in Russian Patent No. 2026857. The alkoxyester is converted to an amide, 2-methoxyisobutanamide (14), for example, by reaction with ammonium hydroxide or ammonia, preferably in methanol. The amide is a white crystalline solid that can easily be stored. It can be reduced into MIBA by methods known in the art, such as by using lithium aluminum hydride, preferably in THF or diethyl ether. Suitable reaction conditions are described in U.S. Pat. No. 4,988,827 and European Patent No. 233368; Russian Patent No. 2026857 and Tarbell et al., *J. Am. Chem. Soc.*, 1950, 72, 2657-2661. These reactions are shown below.

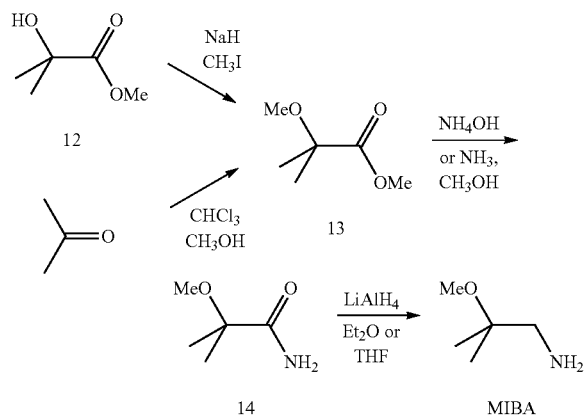

e. Alternative Method 5

MIBA can be prepared by the reduction of 2-methoxy-2-methyl-1-nitro-propane (15), for example, by using lithium aluminum hydride.

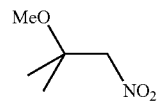

Compound (15) can be prepared in three steps starting from the condensation of acetone and nitromethane. Suitable conditions are described in Thipyapung et al., *J. Scient. Res. Chulalongkorn Univ.*, 2003, 28(2), 111-118. The reactions are shown below.

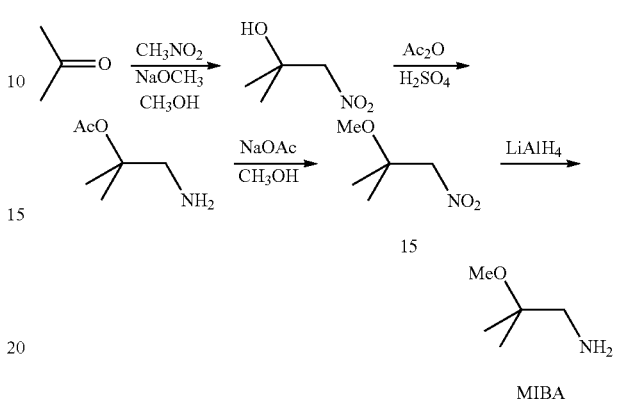

f. Alternative Method 6

MIBA can be prepared from commercially available 2-methylallylamine hydrohalide (such as hydrochloride) and its free base. The ammonium salt can be reacted in an oxymercuration reduction reaction, for example, using mercuric acetate and sodium borohydride in methanol, to form MIBA. Suitable reaction conditions are described in Ferro-Flores et al., *J. Radioanal. Nucl. Chem.*, 1994, 188(6), 409-415. The reaction is shown below. This reaction offers the advantage of involving a single reaction step, although 2-methylallylamine hydrochloride is an expensive reagent, and mercury is produced as waste.

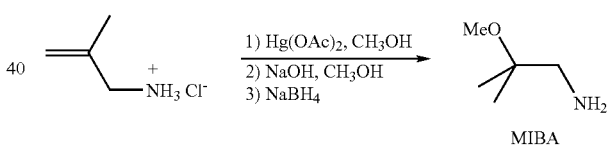

C. Methods of Preparing N-(2-methoxyisobutyl)formamide (MIBF)

MIBA has been observed to degrade over time, therefore it is preferred that it is converted to a more stable derivative or salt. MIBF can be stored for more than one year when kept under argon at 5° C.

1. Preparation via an Ammonium Salt Intermediate

MIBF can be prepared from the N-formylation of a compound of the formula

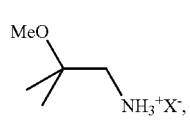

(4)

where X is a halogen, for example, with methyl formate. Compound (4) can be prepared by the acidification of MIBA with a hydrogen halide, such as hydrochloric acid or hydrobromic acid. A preferred method of preparing compound (4) is by reacting MIBA with hydrochloric acid (preferably as a gas) in hexanes. The reaction is shown below

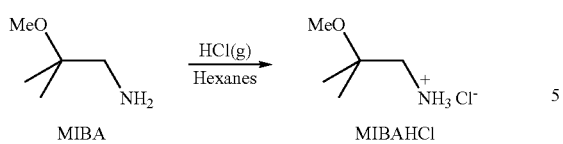

2. Alternative Methods for Preparing MIBF a. Alternative Method 1

MIBF can also be prepared by N-formylation of MIBA, for example, with either formic acid and acetic anhydride or methyl formate or ethyl formate, preferably in the presence of a catalytic amount of para-toluenesulphonic acid. Suitable conditions for these reactions are described in U.S. Pat. Nos. 4,864,051 and 4,988,827, European Patent No. 233368, GB Patent Publication Nos. 2222403(A1) and 2222403(B2); Ramalingham, *Org. Prep. Proced. Int.*, 1989, 21(4), 511-514; German Democratic Republic Patent Publication No. 300742; Slovakian Patent No. 279625; Luo et al., *He Huaxe Yu Fangshe Huasue*, 1992, 14(1), 44-48, 58 and Thipyapung et al., *J. Scient. Res. Chulalongkorn Univ.*, 2003, 28(2), 111-118. Examples of this reaction are shown below.

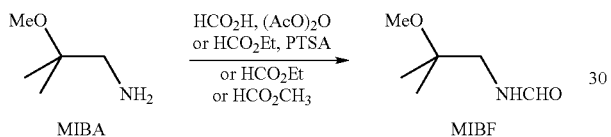

b. Alternative Method 2

MIBF can also be prepared from 2-methylallylamine and 2-methylallylamine hydrohalide (such as hydrochloride). The amine (or the ammonium salt) is formylated, for example, by reaction with either ethyl formate or formamide, preferably in the presence of triethylamine, to provide N-(2-methylallyl)formamide (15). Compound (15) is then subjected to an oxymercuration reduction reaction, for example, using mercuric acetate and sodium borohydride, preferably in methanol, to form MIBF. Suitable reaction conditions are described in *IAEA-TECDOC*-532; Manta, *IAEA-TECDOC*-805, 1995 and Van Wyk et al., *Appl. Radial. Isot.*, 1991, 42, 687-689, 1989. The reactions are shown below.

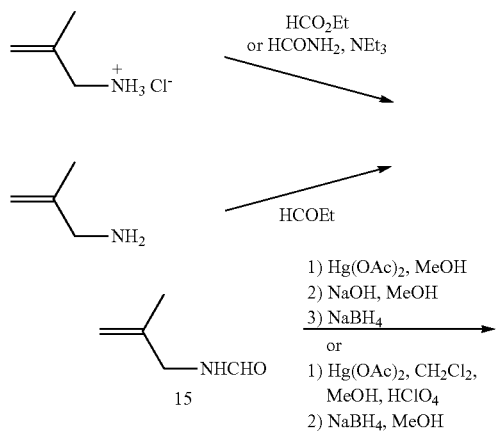

c. Alternative Method 3

MIBF can be prepared from (2-methyl-propenyl)-formamide. This compound can be produced by the N-formylation of 2-methyl-propenylamine hydrochloride with formamide under microwaving conditions. Suitable conditions for this reaction are described in Lima et al., *Brazilian Archives of Biology and Technology*, 2005, 48, 1-8. The reactions are shown below.

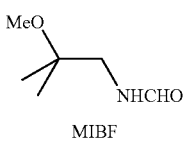

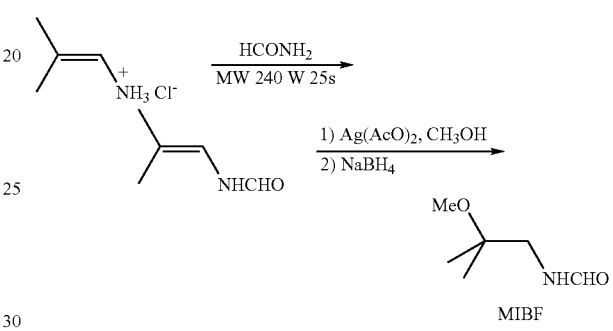

D. Methods of Preparing 2-methoxyisobutylisonitrile (MIBI)

1. Preparation of MIBI from MIBF

MIBF can be converted to MIBI by dehydration of the formamide group, for example, with 2,4,6-trichloro[1,3,5]triazine, also known as TCT or cyanuric chloride. Preferably, the reaction is performed in the presence of a base, such as triethylamine, in a chlorinated solvent, such as dichloromethane. Formation of MIBI is clearly confirmed by its characteristic odor as soon as the formamide is mixed with the dehydrating agent (TCT). For example, reacting one equivalent of MIBF with one equivalent of TCT and two equivalents of anhydrous triethylamine in anhydrous dichloromethane produces MIBI. The reaction occurs from low temperatures to refluxing dichloromethane. MIBF can also be dehydrated by a process involving microwaving as described in A. Porcheddu et al., *J. Org. Chem.*, 2005, 70, 2361-2363. For example, the aforementioned reaction can be heated in an 800 W microwave oven for 38 seconds in a sealed vial and produces MIBI. The reaction is shown below.

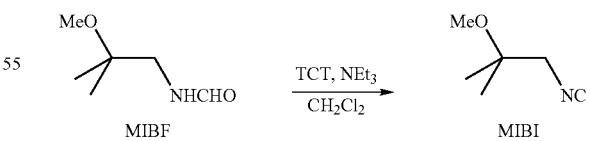

2. Alternative Methods for Preparing MIBI a. Alternative Method 1: Preparing MIBI From MIBF

MIBI can be prepared by the dehydration of MIBF. In one suitable dehydration method, MIBF is reacted with a dehydrating agent such as phosgene, triphosgene (trichloromethyl chloroformate), phosphorus oxychloride or para-toluenesulphonic chloride optionally in the presence of a base (e.g., triethylamine, isopropylamine or pyridine). In another dehydration method, MIBF is reacted with a carbene, which is generated in situ, for example, from the reaction of triphenylphosphine and carbon tetrachloride, preferably in the presence of a base (e.g., triethylamine or isopropylamine) and a solvent (e.g., dichloromethane or chloroform). Suitable reaction conditions are described in European Patent No. 233368, U.S. Pat. Nos. 4,864,051 and 4,988,827; GB Patent Publication Nos. 2222403(A1) and 2222403(B2); Manta, IAEA-TECDOC-805, 1995; Van Wyk et al., *Appl. Radial. Isot.*, 1991, 42, 687-689; K. Ramalingham, *Org. Prep. Proced. Int.*, 1989, 21(4), 511-514; German Democratic Republic Patent Publication No. 300742; Slovakian Patent No. 279625; Luo et al., *He Huaxe Yu Fangshe Huasue*, 1992, 14(1), 44-48, 58; IAEA-TECDOC-532, 1989; Thipyapung et al., *J. Scient. Res. Chulalongkorn Univ.*, 2003, 28(2), 111-118 and Lima et al., *Brazilian Archives of Biology and Technology*, 2005, 48, 1-8. MIBF can be prepared by any method, including those discussed herein. These reactions are shown below.

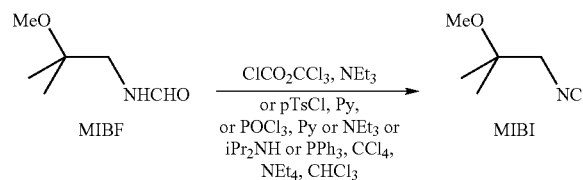

b. Alternative Method 2: Preparing MIBI From MIBAMIBI can also be prepared from MIBA through a Carbylamine reaction. MIBA is reacted with a carbene generated in situ, for example, from the reaction of a strong base (e.g., sodium or potassium hydroxide) with chloroform, preferably in dichloromethane and optionally using triethylbenzylammonium chloride (TEBAC) or trimethylbenzylammonium chloride (TMBAC) as a phase transfer catalyst. Suitable reaction conditions are described in Ferro-Flores et al., *J. Radioanal. Nucl. Chem.*, 1994, 188(6), 409-415; U.S. Pat. Nos. 5,210,270 and 5,346,995; European Patent No. 546233(B1); Te-Wei et al., *Appl. Radial. Isot.*, 1996, 47(2), 207-210; Slovakian Patent No. 280287(B6) and Czech Patent No. 286794 (B6); Zykov et al., *J. Radioanal. Nucl. Chem.*, 1997, 221(1-2), 227-229. The reactions are shown below.

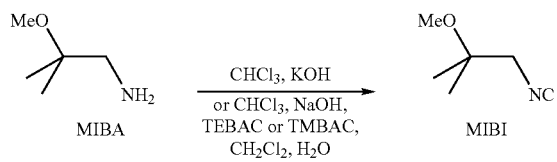

E. Methods of Preparing Tetrakis(2-Methoxyisobutylisonitrile)Copper(I) tetrafluoroborate (CuMIBI)

1. Preparation of CuMIBI from Cuprous Chloride

CuMIBI can be formed from cuprous chloride. CuCl can be reacted with MIBI, for example, in refluxing ethanol under normal conditions of temperature and pressure, to form [Cu(MIBI)$_4$]Cl. The product can be reacted in an anion exchange with a water soluble tetrafluoroborate salt (such as sodium tetrafluoroborate) to form [Cu(MIBI)$_4$]BF$_4$. The product can be purified by any method, such as precipitation from a hot solution in ethanol poured into diethyl ether (or pentane or hexane). The process can be safely scaled-up. CuMIBI can be stored at least one year at room temperature protected from direct light under an inert atmosphere (such as argon) without significant degradation. The reaction is shown below.

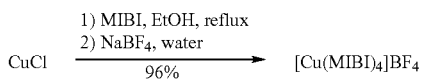

Reactions starting from CuCl were previously reported to have been performed in screw capped vials or bottles, which means under high pressure. Only one reference, Deicas et al., *Polyhedron*, 1997, 16(14), 2397-2403, discloses reactions involving CuCl and ammonium tetrafluoroborate (versus sodium tetrafluoroborate) performed at room temperature (versus refluxing ethanol). Their yield was lower than that of the present invention described in the prior paragraph (50% compared to 96%). Deicas purified by crystallization rather than precipitation, which is time and yield consuming compared to the present process.

2. Alternative Methods of Preparing CuMIBI

Five syntheses of CuMIBI from MIBI have been reported. These methods are described in detail below.

a. Alternative Method 1

CuMIBI can be prepared by the thermal heating of cuprous chloride with MIBI, preferably in anhydrous ethanol e.g., in a sealed container, such as in screw capped vials or bottles, followed by precipitation with a tetrafluoroborate salt (e.g., sodium tetrafluoroborate). CuMIBI can be purified by any method, such as crystallization from a mixture of ethanol and diethyl ether. Suitable reaction conditions are described in IAEA-TECDOC-805, 1995, German Democratic Republic Patent Publication No. 300742; Slovakian Patent No. 279625 and Thipyapung et al., *J. Scient. Res. Chulalongkorn Univ.*, 2003, 28(2), 111-118. The reaction is shown below.

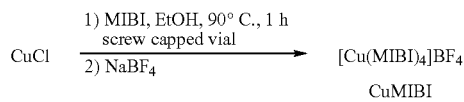

b. Alternative Method 2

CuMIBI can be prepared by reacting cuprous chloride and MIBI at room temperature, preferably in anhydrous ethanol, followed by precipitation with a tetrafluoroborate salt (e.g., ammonium or sodium tetrafluoroborate). CuMIBI can be purified by any method, such as crystallization from a mixture of ethanol and diethyl ether. Suitable reaction conditions are described in Deicas et al., Polyhedron, 1997, 16(14), 2397-2403; Zykov et al., *J. Radioanal. Nucl. Chem.*, 1997, 221(1-2), 227-229 and Lima et al., *Brazilian Archives of Biology and Technology*, 2005, 48, 1-8. The reaction is shown below.

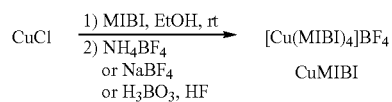

c. Alternative Method 3

CuMIBI can be prepared by reacting CuCl with a water soluble tetrafluoroborate salt (e.g., NaBF$_4$) and MIBI at 0° C. in 1N HCl. Suitable reaction conditions are described in Slovakian Patent No. 279625(B6) and German Democratic Republic Patent Publication No. 300742. The reaction is shown below.

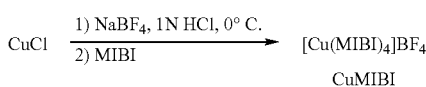

d. Alternative Method 4

CuMIBI can be prepared by reacting cuprous tetrafluoroborate and MIBI heated under reflux, preferably in anhydrous ethanol. Suitable reaction conditions are described in Luo et al., *He Huaxue Yu Fangshe Huasue*, 1992, 14(1), 44-48, 58. The reaction is shown below. $CuBF_4$ can be made by methods known in the art.

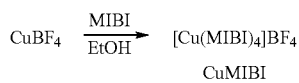

e. Alternative Method 5

CuMIBI can be prepared by reacting tetrakis(acetonitrile)copper(I) tetrafluoroborate ($[Cu(NCMe)_4]BF_4$) with MIBI, preferably in anhydrous ethanol at room temperature. CuMIBI can be purified by any method, such as crystallization from a mixture of ethanol and n-hexane. Suitable reaction conditions are described in U.S. Pat. Nos. 5,210,270 and 5,346,995; European Patent No. 546233(B1); and Te-Wei et al., *Appl. Radiat. Isot.*, 1996, 47(2), 207-210. The reaction is shown below. $[Cu(NCMe)_4]BF_4$ can be made by methods known in the art.

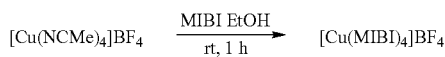

Preferred Syntheses

According to one preferred embodiment, MIBI is prepared from 2,2-dimethyloxirane, which is commercially available and inexpensive. 2,2-Dimethyloxirane is converted into 2-methoxyisobutanol (MIBOL) by a ring opening reaction in methanol in the presence of a catalytic amount of sulfuric acid. MIBOL is reacted in a Mitsunobu or Mitsunobu/Staudinger reaction to form 2-methoxyisobutylamine (MIBA).

Preferably, MIBA is converted to 2-methoxyisobutylisonitrile (MIBI) in the following manner. MIBI is converted to 2-methoxyisobutylamine hydrochloride (MIBAHCl) with hydrochloric acid gas in hexanes. MIBAHCl is N-formylated with methyl formate to produce N-(2-methoxyisobutyl)formamide (MIBF). The formamide derivative is dehydrated using $POCl_3$ or cyanuric chloride (TCT) to provide 2-methoxyisobutylisonitrile (MIBI). Alternatively, other methods in the art, such as those described above, may be employed to convert MIBA or MIBF to MIBI.

According to a second preferred embodiment, the invention provides a method of preparing MIBI starting from 1-chloro-2-methyl-propan-2-ol. The halide is first reacted with potassium phthalimide to produce N-(2-hydroxyisobutyl)-phthalimide, which is reacted with dimethylcarbonate to methoxylate the tertiary alcohol group under green conditions to form N-(2-methoxyisobutyl)-phthalimide. The phthalimide group is then cleaved off by hydrazinolysis to produce MIBA. It is also preferred that MIBA be converted to MIBI as described above; however, alternative methods, such as those described below, are also acceptable.

These new syntheses of MIBI offer the advantages of reagents that are readily available and relatively inexpensive, high yields, the capability of storing the intermediates MIBAHCl and MIBF, the ease of scaling-up, and the lack of highly toxic waste, such as mercury.

According to another embodiment, CuMIBI is prepared from MIBI under mild conditions and at about atmospheric pressure, without time-consuming purification, which can be readily scaled-up. CuCl with MIBI are reacted by thermal heating in anhydrous ethanol, followed by precipitation of $[Cu(MIBI)_4]BF_4$ from an anion exchange with sodium tetrafluoroborate in aqueous media. $[Cu(MIBI)_4]BF_4$ is purified by precipitation in diethyl ethyl (or pentane or hexane) from a solution in ethanol. This process provides $[Cu(MIBI)_4]BF_4$ in a yield of around 96% with a purity of greater than 99%. This process can be safely scaled up.

These preferred embodiments are shown in the following reaction schemes.

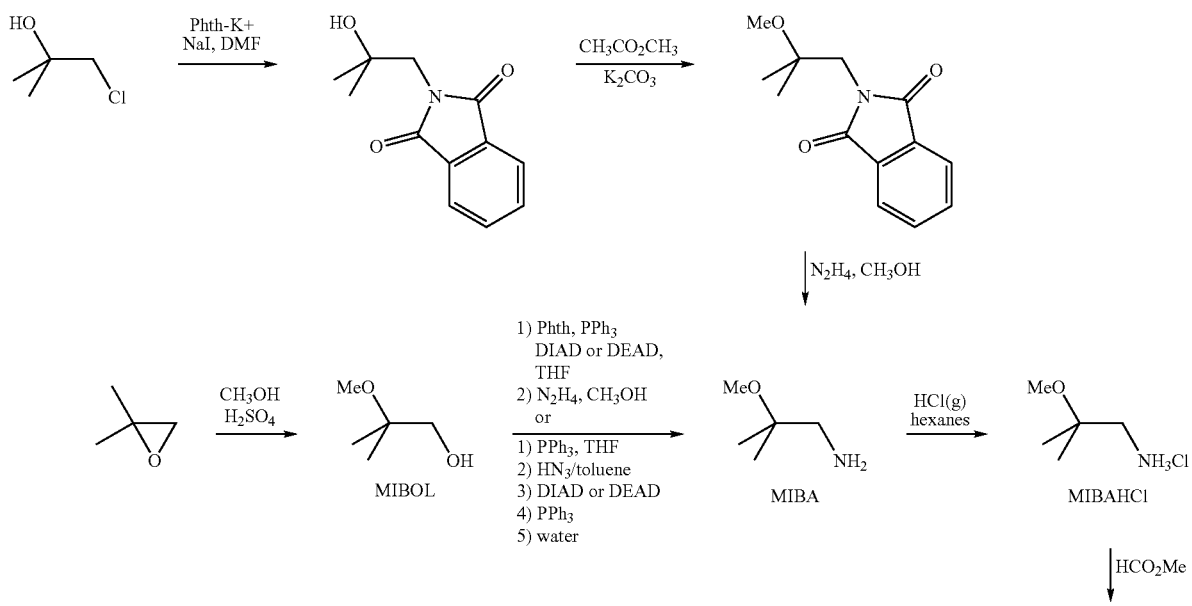

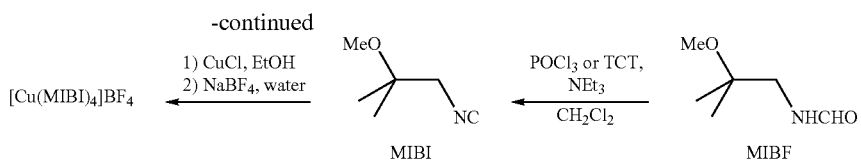

The following examples are provided by way of illustration and do not limit the invention as set forth in the claims.

EXAMPLES

Materials and General Procedures For Examples 1-9

All reactions were carried out under an atmosphere of dry argon unless otherwise specified. Reagents were obtained from Aldrich Chemical Co, VWR international, Fisher Scientific and American Chemicals Inc. and used without further purification. Cuprous chloride was purchased from Aldrich Chemical Co at 99.995% pure based on metal analysis and assayed in Cu(1) with cerium (IV). Tetrahydrofuran was purified by distillation on benzophenone-sodium under argon. Dichloromethane and DMF were distilled from $CaH_2$ under argon. Ethanol was distilled from sodium under argon. TLC was performed using Sigma-Aldrich silica gel F-254 on aluminum plates (200 μm thickness, 60 Å pore size, with fluorescent indicator) except for CuMIBI, which was analyzed on Baker-flex® Aluminum Oxide IB-F.TLC plate. Solvent systems are reported as v/v mixtures. Compounds were visualized using 254 nm UV light, or a solution of p-anisaldehyde followed by heating with a heat gun, or a 0.2% w/w solution of ninhydrine in ethanol followed by heating with a heat gun or a 0.05% w/w solution of dithizone in dichloromethane, or by trituration in a 2% w/w mixture of iodine and silica gel. Sorbent Technologies GF-TLC silica gel (5-15 μm, 60 Å) and Silicycle silica gel (230-400 mesh, 60 Å) were used for preparative thin-layer chromatography and flash chromatography respectively. Melting points were determined on a Thomas Hoover capillary melting point apparatus. The NMR spectra were recorded at ambient temperature on Bruker AV-600 and DRX 500 spectrometers with TBI and BBI probes respectively. Chemicals shifts (δ) are relative to tetramethylsilane as internal standard for $^1$H-NMR, and $CFCl_3$ and $BF_3.OEt_2$ as external references for $^{19}$F-NMR and $^{11}$B-NMR respectively. EI refers to electron impact mass spectrometry and CI refers to chemical ionization mass spectrometry. EI and CI were performed on a Waters Micromass GCT Time-of-Flight mass spectrometer. FTIR spectra were acquired in transmission on Perkin-Elmer 1600 Series and Spectrum 100 spectrometers using round sodium chloride crystal windows for liquids and infrared grade potassium bromide substrate for solids. GC analyses were performed on a Hewlett Packard (HP6890) gas chromatogram equipped with split/splitless injector and flame ionization detector (FID). HPLC analyses were performed on a Hewlett Packard Series 1100 HPLC. Radioactive samples were detected on a Shell Jr 1000 Gamma/PET radio-HPLC scintillation detector using a 10 μL liquid flowcell and ⅛" lead shielding for the NaI detector.

Example 1

Synthesis of 2-Methoxyisobutanol (MIBOL)

A solution of 2,2-dimethyloxirane (148.68 g, 2 mol) in methanol (700 mL) was added dropwise to a solution of concentrated sulfuric acid (46 mg) in methanol (10 ml) proceeding under air. The solution was heated under reflux for 4 hours and then cooled to room temperature. Using a pH meter, the pH was adjusted to 7 with a potassium hydroxide solution in methanol (prepared from 3 g of potassium hydroxide in 10 mL of methanol) and eventually a sulfuric acid solution in methanol (prepared from 1 drop of concentrated sulfuric acid in 10 mL of methanol). The solution was distilled at atmospheric pressure on a Vigreux column yielding MIBOL as a colorless liquid (187.08 g, 90%, b.p.: 137.5-139.0° C.). TLC $R_f$ 0.35 (3:2 ethyl acetate/hexanes, detection with p-anisaldehyde spray); FTIR (neat): ν 3441 (OH st), 2973, 2938, 2828, 1467, 1365, 1275, 1241, 1181, 1156, 1078, 1007, 976, 891, 857, 736 cm$^{-1}$; $^1$H-NMR (600 MHz, $CDCl_3$): δ 1.10 (s, 6H, 2 $CH_3$), 2.40 (s, 1H, OH), 3.17, (s, 3H, $OCH_3$), 3.37 (s, 2H, $CH_2$); $^{13}$C-NMR (151 MHz, $CDCl_3$): δ 21.3 (2 $CH_3$), 49.4 ($OCH_3$), 69.2 ($CH_2$), 75.2 (C).

Example 2

Synthesis of 2-(2-Hydroxyisobutyl)-Phthalimide

A solution of 1-chloro-2-methyl-2-propanol (2.23 g, 97%, 0.02 mol), potassium phthalimide (3.780 g, 98%, 0.02 mol) and sodium iodide (60 mg, 4 mmol) in anhydrous DMF (40 mL) was heated to reflux overnight. The solvent was evaporated under reduced pressure. The resulting product was triturated with a mixture of 3:2 ethyl acetate/hexanes and the ensuing white precipitate was removed by filtration. The yellow filtrate was concentrated under reduced pressure and purified by flash chromatography in a mixture of 2:3 ethyl acetate/hexanes. The impure product thus isolated was triturated with hot hexanes (125 mL) and filtered to remove an insoluble white impurity. After evaporation of the solvent under reduced pressure, the obtained white solid was recrystallized in hexanes. The product was yielded as colorless crystals that were collected by filtration and dried under high vacuum (1.63 g, 37% yield). m.p.: 104-105° C.; TLC $R_f$ 0.20 (2:3 ethyl acetate/hexanes); FTIR (KBr): 3524, 3456, 3097, 3031, 2973, 2930, 1773, 1698, 1611, 1466, 1427, 1389, 1319, 1190, 1076, 990, 965, 912, 890, 838, 766, 724, 712, 638 cm$^{-1}$; $^1$H-NMR (500 MHz, $CDCl_3$): δ 1.26 (s, 6H, 2 $CH_3$), 2.74 (s, 1H, OH), 3.75 (s, 2H, $CH_2$), 7.72 (dd, 2H, $J_o$=5.44 Hz, $J_m$=3.04 Hz, 2 $H_c$), 7.85 (dd, 2H, $J_o$=5.42 Hz, $J_m$=3.06 Hz, 2 $H_b$); $^{13}$C-NMR (126 MHz, $CDCl_3$): δ 27.6 (2 $CH_3$), 49.3 ($CH_2$), 71.6 ($CMe_2$), 123.6 (2 $C_b$), 132.0 (2 $C_a$), 134.3 (2 $C_c$), 169.3 (2 CO).

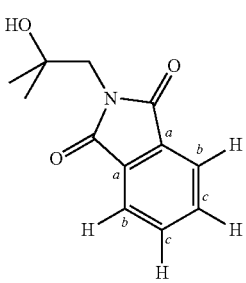 [SMILES: CC(C)(O)CN1C(=O)c2ccccc2C1=O]

Example 3

Synthesis of N-(2-Methoxyisobutyl)-Phthalimide

A solution of N-(2-hydroxyisobutyl)-phthalimide (258 mg, 1.18 mmol), potassium carbonate (325 mg, 2.35 mmol) and dimethylcarbonate (2.12 g, 23.52 mmol) in a 5 mL screw-cap reacti-vial was heated at 200° C. for 2 hours in an oil bath. The solution was evaporated to dryness under reduced pressure and the resulting product, a white solid, was purified by preparative thin layer chromatography using an eluent composed of 1:4 ethyl acetate/hexanes. The TLC silica gel was extracted with $CH_2Cl_2$ and ethyl acetate. After evaporation under reduced pressure, the resulting white solid was recrystallized in hexanes yielding the product as colorless crystals (45 mg, 16% yield). m.p.: 99-100° C.; TLC $R_f$ 0.36 (2:3 ethyl acetate/hexanes); FTIR(KBr): 3469, 3068, 3031, 3002, 2956, 2841, 1776, 1750, 1710, 1614, 1468, 1430, 1389, 1276, 1205, 1168, 1081, 994, 966, 933, 906, 877, 788, 726, 713, 638 cm$^{-1}$; $^1$H-NMR (500 MHz, CDCl$_3$): δ 1.51 (s, 6H, 2 CH$_3$), 3.79 (s, 3H, OCH$_3$), 4.10 (s, 2H, CH$_2$), 7.71 (dd, 2H, J$_o$=5.46 Hz, J$_m$=3.04 Hz, 2H$_c$), 7.85 (dd, 2H, J$_o$=5.42 Hz, J$_m$=3.06 Hz, 2 H$_b$); $^{13}$C-NMR (126 MHz, CDCl$_3$): δ 24.7 (2 CH$_3$), 44.5 (CH$_2$), 54.3 (OCH$_3$), 82.8 (CMe$_2$), 123.6 (2 C$_b$), 132.1 (2 C$_a$), 134.2 (2 C$_c$), 168.6 (2 CO).

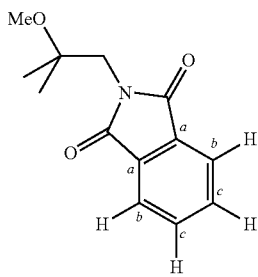 [SMILES: COC(C)(C)CN1C(=O)c2ccccc2C1=O]

Example 4

Synthesis of 2-Methoxyisobutylamine (MIBA)

Method 1

Diisopropylazodicarboxylate (524.38 g, 2.48 mol) was added dropwise to a solution of phthalimide (364.77 g, 2.48 mol), triphenylphosphine (652.84 g, 2.48 mol), and MIBOL (220.07 g, 97.7% (GC), 2.06 mol) in anhydrous tetrahydrofuran (10815 mL). A duplicate solution was prepared. The solutions were stirred for a minimum of 3 hours and the reaction was monitored by TLC analysis (2:3 ethyl acetate/hexanes, detection with 254 nm UV light and p-anisaldehyde spray). When the disappearance of MIBOL was confirmed, the solvent was removed by rotary evaporation under reduced pressure and the reaction mixtures were combined. The resulting orange oil was triturated with hexanes (4275 mL) until obtaining a semi-solid. The solvent was removed by rotary evaporation under reduced pressure and the crude solid was dried under high vacuum. The solid was suspended in methanol (7875 mL) and hydrazine monohydrate (413.26 g, 8.26 mol) was added. The solution was heated to reflux with mechanical stirring. An additional portion of methanol (2000 mL) was added after 25 minutes of reflux to increase the fluidity of the suspension. After 45 minutes of reflux, disappearance of the phthalimide intermediate was confirmed by TLC analysis (R$_f$ 0.4, 2:3 ethyl acetate/hexanes, detection with 254 nm UV light and p-anisaldehyde spray). The solution was cooled to room temperature. A solution of concentrated hydrochloric acid (609 mL) and methanol (609 mL) was added, and the solution was heated at reflux for 9 hours with magnetic stirring. After cooling to room temperature, the solution was filtered on Celite® and the residue rinsed portionwise with methanol (5960 mL). The filtrate was evaporated under reduced pressure and dried under high vacuum. The product, a yellow solid, was triturated five times with 1N hydrochloric acid (3600 mL, 2925 mL and 3 times 2250 mL). The fractions were combined and concentrated to 4645 mL by rotary evaporation under reduced pressure. The resulting solution was split in two batches of equal volume. Each batch was extracted with ethyl acetate (twice 640 mL). The aqueous layers were combined and concentrated to 4500 mL by rotary evaporation under reduced pressure. The resulting solution was basified to a pH of 11 by carefully adding pellets of sodium hydroxide (1427 g) yielding a green olive, almost black, extremely viscous oily solution. It was filtered and the residue rinsed with diethyl ether (3370 mL). The solution was extracted continuously three times with diethyl ether. The organic layer (18050 mL) resulting from the liquid-liquid extraction was dried over anhydrous MgSO$_4$. The solution was distilled at atmospheric pressure on a Vigreux column yielding MIBA as a colorless liquid (299.51 g, 70% yield, 97.0% (GC), b.p.: 120.0-120.5° C.). TLC R$_f$ 0.5 (90:9.75:0.25 CH$_2$Cl$_2$/CH$_3$OH/NH$_4$OH, detection with ninhydrine spray); FTIR(neat): 3386, 3314, 2971, 2935, 2826, 1597, 1468, 1381, 1364, 1306, 1259, 1223, 1195, 1155, 1118, 1074, 1013, 894, 847, 716 cm$^{-1}$; $^1$H-NMR (600 MHz, CDCl$_3$): δ 1.13 (s, 6H, 2 CH$_3$), 2.62 (s, 2H, CH$_2$), 3.19 (s, 3H, OCH$_3$), 4.76 (br s, 2H, NH$_2$); $^{13}$C-NMR (151 MHz, CDCl$_3$): δ 22.6 (2 CH$_3$), 49.4 (OCH$_3$), 50.6 (CH$_2$), 75.0 (C).

Method 2

N-(2-Methoxyisobutyl)-phthalimide (1 eq) was reacted with hydrazine monohydrate (4 eq) in methanol and yielded MIBA following a similar procedure as described in method 1.

Example 5

Synthesis of 2-Methoxyisobutylamine Hydrochloride (MIBAHCl)

Hydrochloric acid generated from concentrated sulfuric acid and sodium chloride (or from dripping of concentrated hydrochloric acid over concentrated sulfuric acid), was bubbled through a solution of MIBA (298.73 g, 97.0% (GC), 2.81 mmol) in hexanes (7160 mL) until most of the forming MIBAHCl solubilizes. The solvent was carefully removed by rotary evaporation under reduced pressure. The obtained product, a white solid, was dried under high vacuum and triturated in hot hexanes (2860 mL). MIBAHCl was filtered off under a blanket of argon and yielded as a white solid (386.88 g, 99.0% (GC), 98% yield). The title compound is highly hygroscopic and should be stored in a dessicator. m.p.: 121-123° C.; TLC R$_f$ 0.5 (90:9.75: 0.25 CH$_2$Cl$_2$/CH$_3$OH/NH$_4$OH, sample diluted in a mixture of 1 mL:1 drop CH$_3$OH/28% NH$_4$OH, detection with ninhydrine spray); FTIR(KBr): 3426, 2978, 2692, 2596, 2008, 1618, 1499, 1476, 1396, 1374, 1329, 1264, 1206, 1177, 1096, 1057, 1013, 949, 871, 841, 720 cm$^{-1}$; $^1$H (600 MHz, CDCl$_3$): δ 1.20 (s, 6H, 2 CH$_3$), 2.91 (q, 2H, J=5.9 Hz, CH$_2$), 3.14 (s, 3H, OCH$_3$), 8.21 (br s, 3H, NH$_3^+$); $^{13}$C-NMR (151 MHz, CDCl$_3$): δ 22.5 (2 CH$_3$), 47.9 (CH$_2$), 49.5 (OCH$_3$), 72.0 (C).

Example 6

Synthesis of N-(2-Methoxyisobutyl)formamide (MIBF)

A suspension of MIBAHCl (220.00 g, 99.0% (GC), 1.56 mol) in methyl formate (767.32 g, 12.73 mol) was heated to reflux, and triethylamine (175.39 g, 1.73 mol) was added dropwise. The reaction mixture was heated to reflux. The reaction was monitored by TLC until disappearance of MIBAHCl. After 68 hours, the resulting white suspension was cooled to room temperature the solution was filtered and the residue rinsed with diethyl ether (2862 mL). The filtrate was concentrated by rotary evaporation under reduced pressure and the product, a yellow oil, was distilled under reduced pressure (1.5 mmHg). MIBF was yielded as a colorless liquid (201.34 g, 98% yield, 99.8% (GC), b.p.: 120.0-120.5° C./1.50 mmHg); TLC R$_f$ 0.2 (4:1 ethyl acetate/hexanes, detection with p-anisaldehyde spray); FTIR(neat): ν 3300, 3061, 2977, 2938, 2831, 2751, 1671, 1534, 1469, 1385, 1368, 1287, 1238, 1183, 1164, 1079, 1034, 1004, 957, 858, 721, 666 cm$^{-1}$; $^1$H-NMR (600 MHz, CDCl$_3$): δ 1.13 (s, 6H, 2 CH$_3$), 3.16 (s, 3H, OCH$_3$), 3.28 (d, J=5.9 Hz, 2H, CH$_2$), 6.12 (br s, 1H, NH), 8.19 (s, 1H, CHO); $^{13}$C-NMR (151 MHz, CDCl$_3$): δ 22.5 (2 CH$_3$), 46.0 (CH$_2$), 49.4 (OCH$_3$), 74.1 (C), 161.4 (CHO); MS (EI): m/z=132[M+H]$^+$; MS (Cl): m/z=132[M+H]$^-$.

Example 7

Synthesis of 2-Methoxyisobutylisonitrile (MIBI)

Method 1

Phosphorus oxychloride (from a fresh unopened bottle, 94 g, 0.61 mol) was added dropwise to a solution of MIBF (73 g, 99.7% (GC), 0.55 mol) and triethylamine (140.91 g, 1.39 mol) in anhydrous dichloromethane (555 mL) maintained between −5° C. and +3° C. The solution was stirred overnight at ice temperature. The reaction was quenched by pouring it carefully into a solution of sodium carbonate (123 g) in water (500 mL) cooled in an ice-water bath. The solution was stirred for 30 minutes in ice and diluted with water (500 mL). The precipitate was filtered off on Celite® and rinsed portionwise with dichloromethane (925 mL). The organic layer was isolated from the filtrate. The remaining aqueous layer was extracted twice with dichloromethane (twice 275 mL). The organic layers were combined and dried over anhydrous sodium sulfate. The solution was filtered and concentrated by rotary evaporation to a volume of 250-300 mL. MIBI was isolated by distillation under reduced pressure (5-6 mmHg) as a colorless liquid (50.49 g, 80% yield, 99.7% (GC), b.p.: 46° C./5-6 mmHg). TLC R$_f$ 0.6 (4:1 ethyl acetate/hexanes, detection with iodine stain) R$_f$ 0.2 (CH$_2$Cl$_2$, detection with iodine stain); FTIR(neat): ν 2983, 2944, 2833, 2152, 1470, 1388, 1370, 1294, 1242, 1184, 1166, 1079, 1010, 991, 945, 879, 857, 744 cm$^{-1}$; $^1$H-NMR (600 MHz, CDCl$_3$): δ 1.23 (s, 6H, 2 CH$_3$), 3.21 (s, 3H, OCH$_3$), 3.33 (m, 2H, $^2$J$_{1H,14N}$=1.8 Hz, CH$_2$); $^{13}$C-NMR (151 MHz, CDCl$_3$): δ 22.4 (2 CH$_3$), 49.9 (OCH$_3$), 50.5 (t, $^1$J$_{13C,14N}$=6.8 Hz, CH$_2$), 73.2 (C), 157.6 (t, $^1$J$_{13C,14N}$=5.3 Hz, N≡C).

Method 2

A solution of cyanuric chloride (2.84 g, 15.3 mmol), MIBF (2.00 g, 15.3 mmol) and anhydrous triethylamine (4.27 mL, 30.5 mmol) in anhydrous dichloromethane (50 mL) was prepared at 0° C. and heated to reflux. The reaction was monitored by GC. After 2 h 30, the presence of MIBI was confirmed by TLC. The isonitrile was produced in 20% yield (GC).

Method 3

A solution of MIBF (50 mg, 0.38 mmol), anhydrous triethylamine (107 uL, 0.76 mmol) and cyanuric chloride (71 mg, 0.38 mmol) in anhydrous dichloromethane (0.5 mL) was prepared at 0° C. under argon in a 1 mL screw-cap reacti-vial. The solution was heated 38 seconds in a 800 W microwave oven (Sylvania model SM8070, 40% power). After cooling to room temperature, formation of MIBI was clearly confirmed by its characteristic odor and TLC analysis.

Example 8

Synthesis of Tetrakis(2-methoxyisobutylisonitrile)copper(I) Tetrafluoroborate (CuMIBI)

MIBI (38.00 g, 99.8%, 335.3 mmol) was added to a suspension of cuprous chloride (8.22 g, 97.8%, 81.2 mmol) in anhydrous ethanol (76 mL). The solution was heated to reflux until the greenish suspension turned into an almost clear yellowish to beige solution. After 7 hours, the solution was cooled to room temperature. The solvent was evaporated in vacuo and the resulting orange oil dried under high vacuum. The resulting off-white solid was dissolved in water (152 mL) and cooled to ice temperature. A solution of NaBF$_4$ (2.2 M, 152 mL) was added. The resulting white suspension was stirred 15 min at 0° C. The white precipitate was collected by filtration, washed portionwise with a solution of NaBF$_4$ (2.2 M, 191 mL), and then water (24 mL) and diethyl ether (282 mL). After drying under high vacuum, the solid was dissolved in hot ethanol (72 mL) and the obtained solution was filtered by gravity into hot diethyl ether (1726 mL) under slow magnetic stirring. [Cu(MIBI)$_4$]BF$_4$ was yielded as white powder that was collected by filtration, rinsed portionwise with diethyl ether (194 mL) and dried under high vacuum (49.25 g, 100% (HPLC), 98% yield). m.p.: 100-101° C. TLC R$_f$ 0.76 (100% ethanol, detection with dithizone spray); FTIR(KBr): ν 3430, 2982, 2948, 2837, 2197, 1636, 1474, 1440, 1390, 1371, 1346, 1298, 1242, 1188, 1167, 1082, 1053, 944, 859, 744, 576, 522, 417 cm$^{-1}$; $^1$H-NMR (600 MHz, CDCl$_3$): δ 1.26 (s, 6H, 2 CH$_3$), 3.23 (s, 3H, OCH$_3$), 3.58 (s, 2H, CH$_2$); $^{13}$C-NMR (151 MHz, CDCl$_3$): δ 22.5 (2 CH$_3$), 50.0 (OCH$_3$), 51.6 (m, $^1$J$_{13C,14N}$=6.6 Hz, CH$_2$), 73.3 (C), 142.4 (N≡C); $^{19}$F-NMR (471 MHz, CDCl$_3$): δ −154.27 (br s or 7-line multiplet, $^{10}$BF$_4^-$), −154.33 (4-line multiplet, $^1$J$_{B-F}$=0.9 Hz, $^{11}$BF$_4^-$); $^{11}$B-NMR (192.5 MHz, CDCl$_3$): δ −1.35 (q, $^1$J$_{B-F}$=0.8 Hz, $^{11}$BF$_4^-$). The $^{19}$F-NMR spectrum showed two peaks at approximately a 1:4 ratio. Under conditions of high resolution, the signal at −154.33 ppm appeared as a four line multiplet, and the signal at −154.27 ppm remained a broad signal. These signals are consistent with the presence of the BF$_4^-$ anion, with an approximately 20:80 ratio of $^{10}$B to $^{11}$B. The higher intensity multiplet can be assigned to the $^{19}$F in $^{11}$BF$_4^-$, with a natural abundance ($^{11}$B) of 80.4% and a nuclear spin of 3/2, resulting in a four line multiplet. The broad singlet of lower intensity can be assigned to the $^{19}$F in $^{10}$BF$_4^-$ with a natural abundance ($^{10}$B) of 19.6% and a nuclear spin of 3, resulting in theory in a seven line multiplet but observed as a broad singlet only.

Example 9

Preparation of $^{99m}$Tc-Hexakis(2-Methoxyisobutylisonitrile)

A 10 mL lyophilized vial containing CuMIBI (1 mg), sodium citrate dihydrate (2.6 mg), L-cysteine hydrochloride monohydrate (1 mg), mannitol (20 mg), and stannous chloride dihydrate (0.075 mg) under nitrogen was reconstituted with 50 mCi of sodium pertechnetate (Tc-99m) for injection in 3 mL saline obtained from the elution of a $^{99}$Mo/$^{99m}$Tc generator. The vial was heated in a boiling water bath for 10 minutes and allowed to cool to room temperature for 15 minutes. The radiochemical purity (RCP) in $^{99m}$Tc-Sestamibi (or $^{99m}$Tc-hexakis(2-methoxyisobutylisonitrile)) was obtained as per the monography for Technetium ($^{99m}$Tc) Sestamibi injection in the United States and European Pharmacopoeia. The RCP was found at 98.7% over a period of 24 hours. The $^{99m}$Tc-impurity, identified as $^{99m}$Tc pentamibi dimethylvinyl isonitrile in the United States Pharmacopoeia, was not detected with 1/8" lead shielding for the NaI detector of the gamma detector.

All non-patent references, patents and patent applications cited and discussed in this specification are incorporated herein by reference in their entirety and to the same extent as if each was individually incorporated by reference.

I claim:

1. A method of preparing 2-methoxyisobutylisonitrile comprising the steps of:
   (a) converting 2,2-dimethyloxirane to 2-methoxyisobutanol,
   (b) converting 2-methoxyisobutanol to 2-methoxyisobutylamine;
   (c) converting the 2-methoxyisobutylamine of step (b) to a compound of the formula

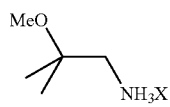
   (4)

where X is halogen, and
   (d) converting the compound of formula (4) to 2-methoxyisobutylisonitrile, wherein step (a) comprises adding 2,2-dimethyloxirane to a solution of acid in methanol, and step (b) comprises:
   (1) reacting 2-methoxyisobutanol with (1) triphenylphosphine, (2) phthalimide, and (3) diethylazodicarboxylate (DEAD) or diisopropylazodicarboxylate (DIAD), to form a compound having the formula

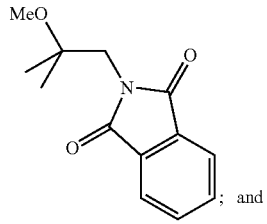 [SMILES: COC(C)(C)CN1C(=O)c2ccccc2C1=O]
   ; and (2) reacting the product of step (1) without purification with hydrazine to form 2-methoxyisobutylamine.

2. The method of claim 1, wherein step (c) comprises reacting 2-methoxyisobutylamine with a hydrogen halide to form the compound of formula (4).

3. The method of claim 2, wherein the hydrogen halide is hydrochloric acid.

4. The method of claim 1, wherein step (d) comprises:
   (I) converting a compound of the formula

   (4)

where X is halogen, to a compound of the formula

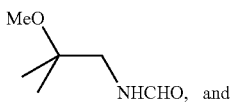
   (5)

(II) converting the compound of formula (5) to 2-methoxyisobutylisonitrile.

5. The method of claim 1, wherein the 2-methoxyisobutylamine of step (b) is subjected to a liquid-liquid extraction prior to step (c).

* * * * *